US 6,588,896 B2

(12) United States Patent
Schleger et al.

(10) Patent No.: US 6,588,896 B2
(45) Date of Patent: Jul. 8, 2003

(54) EYEGLASSES HAVING BIOMAGNETS AND TEMPLE TIPS FOR EYEGLASSES HAVING BIOMAGNETS

(75) Inventors: Stanley Schleger, 535 Dorado Ct., North Hills, NY (US) 11567; Thomas Yang, Elmhurst, NY (US)

(73) Assignee: Stanley Schleger, North Hills, NY (US)

( * ) Notice: Subject to any disclaimer, the term of this patent is extended or adjusted under 35 U.S.C. 154(b) by 0 days.

(21) Appl. No.: 10/083,059

(22) Filed: Feb. 26, 2002

(65) Prior Publication Data

US 2002/0080326 A1 Jun. 27, 2002

Related U.S. Application Data

(62) Division of application No. 09/295,249, filed on Apr. 20, 1999, now Pat. No. 6,375,324.
(60) Provisional application No. 60/094,428, filed on Jul. 28, 1998, and provisional application No. 60/082,655, filed on Apr. 22, 1998.

(51) Int. Cl.⁷ ................................................. G02C 5/14
(52) U.S. Cl. ........................... 351/121; 351/41; 351/111
(58) Field of Search .......................... 351/121, 41, 111, 351/158, 123, 122; 600/9, 15

(56) References Cited

U.S. PATENT DOCUMENTS 6,375,324 B2 * 4/2002 Schleger et al. ............ 351/121

FOREIGN PATENT DOCUMENTS

GB 2246709 * 12/1992

* cited by examiner

Primary Examiner—Hung Xuan Dang
(74) Attorney, Agent, or Firm—Ostrolenk, Faber, Gerb & Soffen, LLP

(57) ABSTRACT

Eyewear comprising a lens for transmitting light to a wearer's eye, a frame for the lens, the frame including temples for supporting the frame on the wearer's ears, the temples comprising a plurality of substantially equally spaced biomagnets or a single strip biomagnet attached to the temples for providing a magnetic field to the wearer's head. Temple tips for attachment to temples of eyewear comprising a longitudinally extending member having a channel therein for receiving the eyewear temple, the temple tips including at least one biomagnet for providing a magnetic field to the wearer's head.

4 Claims, 7 Drawing Sheets

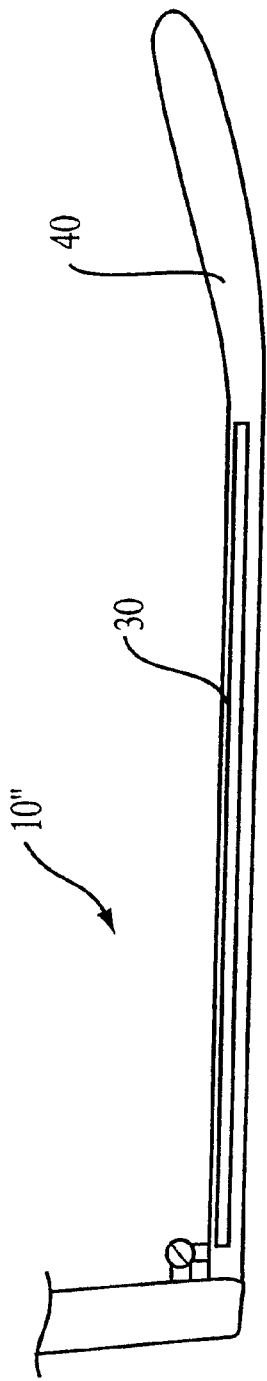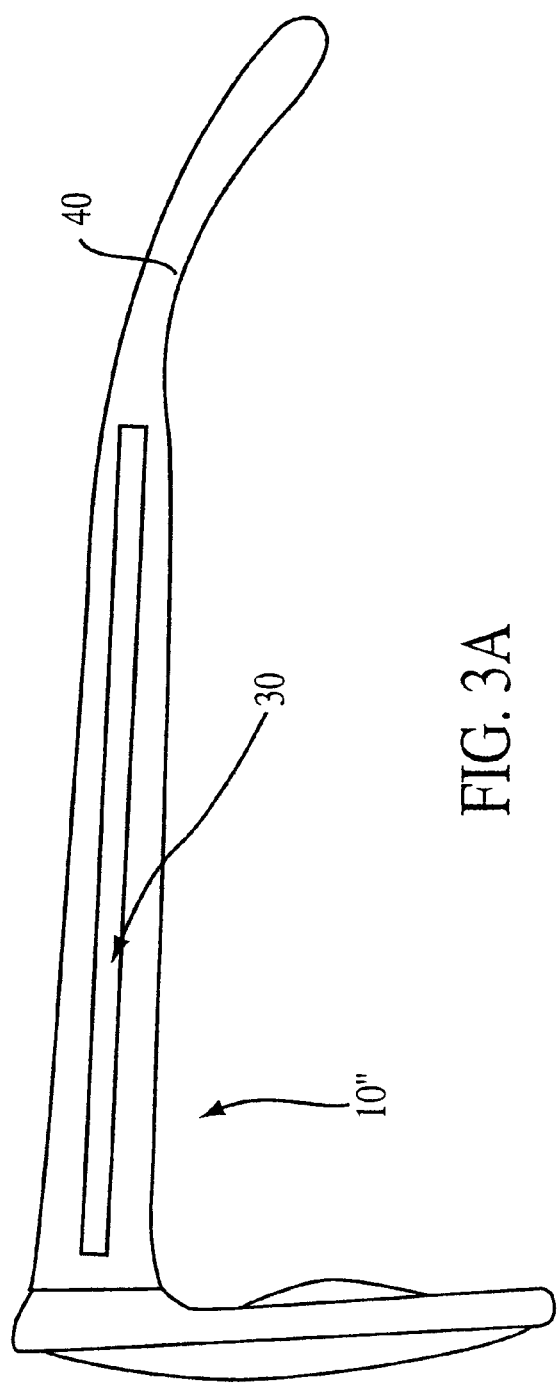
FIG. 3B
FIG. 3A

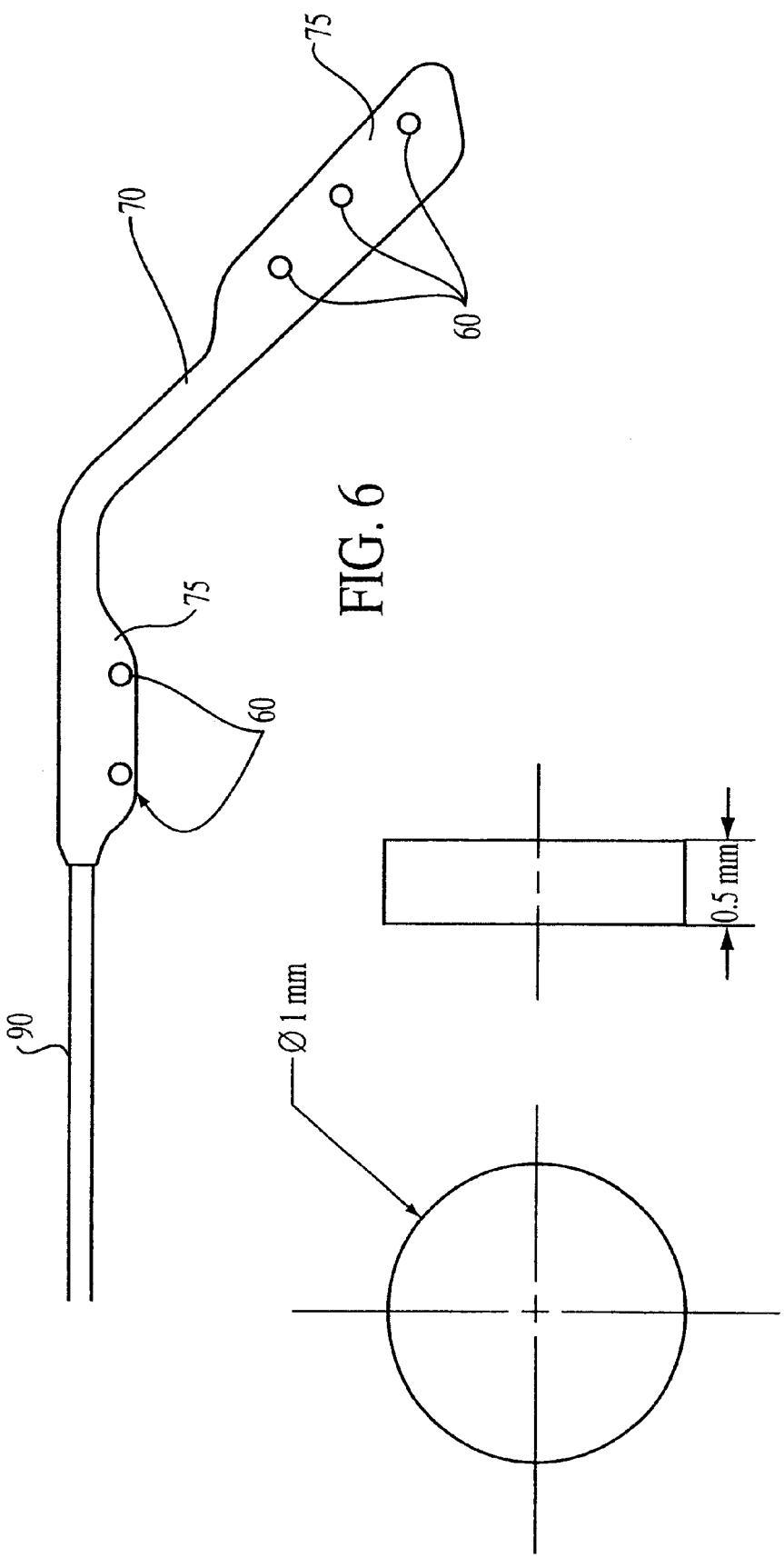

EYEGLASSES HAVING BIOMAGNETS AND TEMPLE TIPS FOR EYEGLASSES HAVING BIOMAGNETS

CROSS REFERENCE TO RELATED APPLICATIONS

This is a division of application Ser. No. 09/295,249, filed Apr. 20, 1999, now U.S. Pat. No. 6,375,324.

This application claims the benefit of provisional application Ser. No. 60/082,655 filed Apr. 22, 1998 and Ser. No. 60/094,428 filed Jul. 28, 1998.

BACKGROUND OF THE INVENTION

The present invention relates to eyeglasses, and in particular, to eyeglasses provided with magnets thereon for providing magnetic therapy to the wearer of the eyeglasses. The invention also relates to temple tips for eyeglasses which include biomagnets. The temple tips can be provided on eyeglasses during manufacture or can be applied on existing eyeglasses to retrofit them with biomagnets.

Today, there are a number of studies and experiments which are being carried forth on the benefits of magnetic therapies. Many people are receiving benefits from magnetic therapies today. In the treatment of sprains, strains, broken bones, and lacerations, magnetic therapies have been used. Magnetic therapies also help in healing and in reducing scar tissue.

A magnet is a lode stone or a body having the property of attracting iron and producing a magnetic field external to itself. There are two poles in a magnet, the north pole and the south pole.

In general, magnetic therapies may increase blood flow by increasing oxygen carrying capacity. Such therapies may also help broken bones to heal in half the usual time by changing the migration of calcium ions. Magnetic therapies have also been used to relieve arthritis pain by moving calcium ions away from painful arthritic joints. Such therapies may also alter the pH level (acidity/alkalinity) of various body fluids that are often out of balance due to illness or abnormal conditions. Magnetic therapies may also increase hormone production from the endocrine gland.

There may be different biological effects caused by a north pole field and a south pole field. It is not exactly known today what the differences are. Biomagnets are often used with a multi-pole or north pole orientation toward the body.

Biomagnets have been designed with a specific strength measured in gauss which falls within a biological therapeutic window.

Applicant is aware of the following references which may be relevant to the field of the invention. DE 3718333, GB 2246709, GB 2257633.

Of interest generally regarding magnetic therapies are U.S. Pat. Nos. 4,095,587 and 5,642,739. Although not prior art, the reader is also directed to recent articles including an article entitled "Study On Using Magnets To Treat Pains Surprises Skeptics", New York Times, Dec. 9, 1997 p.F3, an article entitled "Magnet Passes Test In Relieving Muscle Pain" Staten Island Advance, Dec. 8, 1997 p.D5, an article entitled "Magnets As Medicine", Staten Island Advance, May 4, 1998, p.D1 and an article entitled "Magnets Lessen Foot Pain of Diabetic a Study Finds", New York Times, Jan. 6, 1999, p.A16.

GB 2246709 provides a number of magnets in various parts of eyeglasses to achieve therapeutic effects, in particular to stimulate the nerve areas near the user's eyes. Stimulation is believed to serve to cure or alleviate eye diseases.

GB 2257633 discloses an eyepiece having a spectacle frame made from a compound containing a permanent magnet powder. A magnetic field is created to stimulate the acupuncture and moxibustion points around the face. It is also stated therein that the eyepiece helps correct for errors in the refractory power of the eye.

U.S. Pat. No. 5,643,739 shows a magnetic arm band for applying a magnetic field to target tissues in order to alleviate symptoms of inflammation.

U.S. Pat. No. 4,095,587 discloses a magnetic ornament for promoting good health.

DE 3718333 discloses spectacles having magnets affixed to the frame. The magnets may be located on the sides near the hinge or at the free ends or on the bridge. The magnets are preferably arranged in pairs side-by-side or one above the other. According to this reference, the advantage of the magnets is in the treatment of, for example, bronchitis, colds, headache, concentration problems, etc.

The present inventors believe that there is a need to use biomagnets in medical therapies, and in particular, in therapies relating to reducing headaches resulting from reading books and viewing computer monitors, for example. In addition, applicants believe that there is a need for therapies to lead to better skills for memorizing, making observations and concentrating.

SUMMARY OF THE INVENTION

Accordingly, it is an object of the present invention to provide a means to allow biomagnet therapies to be applied to the human body, and in particular, to the human head area.

In order to achieve the above and other objects, the inventors have developed biomagnetic eyeglasses that include one or more biomagnets thereon to provide biomagnetic therapies to the human body.

According to one aspect of the invention, the invention comprises eyewear comprising at least one lens for transmitting light energy to a wearer's eye, a frame for supporting the lens, the frame including a pair of temples for supporting the eyewear on the wearer's ears, at least one of the temples including a plurality of substantially equally spaced biomagnets disposed integrally in or on the temples for providing a magnetic field to the wearer's head.

According to another embodiment of the invention, at least one of the temples includes a strip biomagnet which is disposed along the longitudinal axis of the temple.

According to another embodiment of the invention, the eyewear includes a frame around an eyepiece which allows light to be transmitted to the wearer's eye, the eyewear including a nose pad for supporting the eyewear on the wearer's nose and further wherein at least one biomagnet is provided at the nose pad to provide the magnetic field to the area near the wearer's nose.

According to another aspect, the invention comprises protective temple tips for attachment to temples of eyewear comprising a longitudinal member having a central channel therein for receiving a temple of eyewear, the temple tips having disposed therein at least one biomagnet for applying a magnetic field to the eyewear wearer's head.

An advantage of the latter invention is that a wearer's eyeglasses can be retrofitted with biomagnets by removing the standard protective temple tips customarily provided and attaching the temple tips according to the invention in place of the standard temple tips. The temple tips according to the invention are preferably made of a pliable material so that they can be bent to the shape of the temples of the eyewear, for example, in the area where the eyewear rest on the ears.

Other features and advantages of the present invention will become apparent from the following description of the invention which refers to the accompanying drawings.

BRIEF DESCRIPTION OF THE DRAWINGS

The invention will now be described in greater detail in the following detailed description with reference to the drawings in which:

FIG. 3A shows a second embodiment of the present invention in a side view;

FIG. 3B shows a partial top view of the second embodiment;

FIG. 6 is a side view of the fourth embodiment showing how the temple tips can be bent to conform to the temples of a wearer's eyewear;

FIG. 6A is a plan view of a suitable biomagnet for use with the temple tips of FIG. 6;

FIG. 6B is a side view of the biomagnet of FIG. 6A; and

DETAILED DESCRIPTION OF EMBODIMENTS OF THE INVENTION

Figure 1:
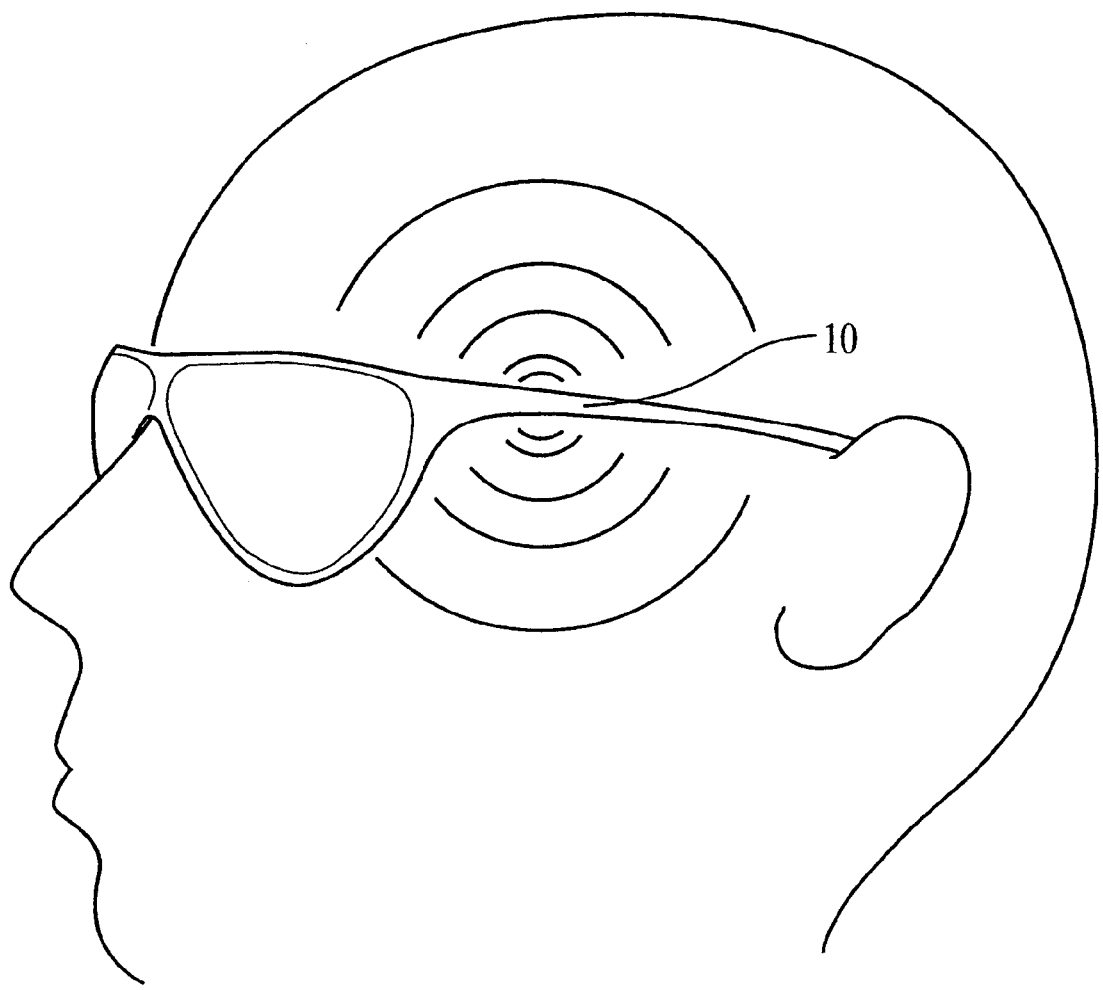
FIG. 1 shows generally how the eyewear according to the present invention applies a magnetic field to the wearer's head.

With reference now to the drawings, the invention comprises eyewear and temple tips for eyewear for providing magnetic therapies to the human body, and in particular, to the head area. FIG. 1 shows generally how the eyewear 10 according to the present invention provided with biomagnets can provide a magnetic field to the wearer's head. According to the invention, the eyewear is especially designed to safely provide the benefits of biomagnet therapy to the human body. Preferably, the biomagnets used in the invention are provided in the frame of the eyewear and in particular, in the temples of the eyewear or near the bridge of the frame of the eyewear. According to one embodiment, the biomagnets are provided in temple tips which can be applied to existing eyewear or used in conjunction with the manufacture of eyewear.

Figure 2A:
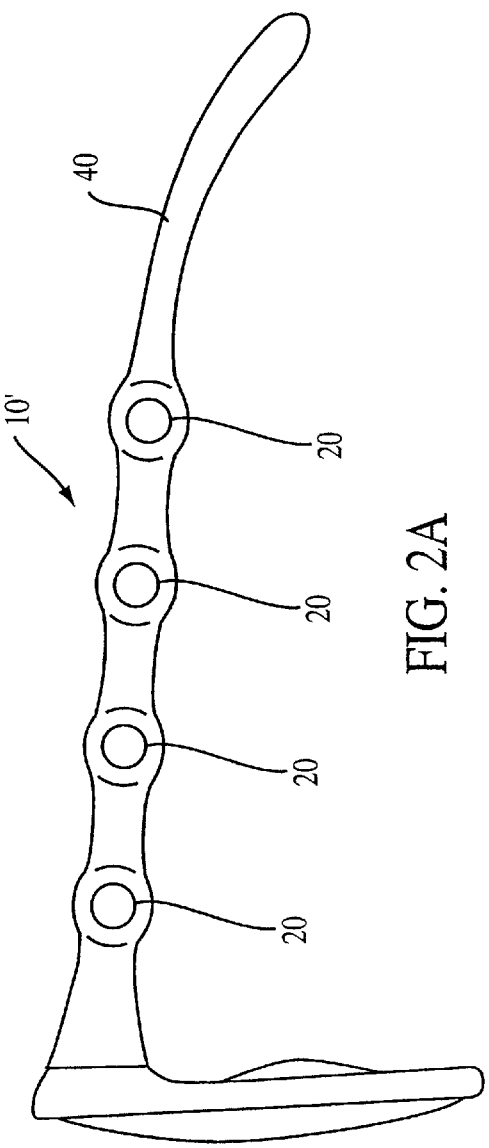
FIG. 2A is a side view of a first embodiment according to the present invention.
Figure 2B:
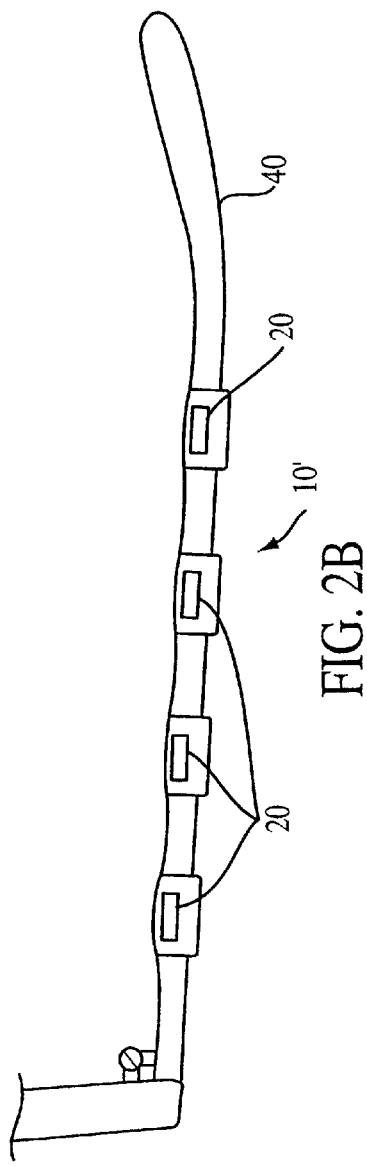
FIG. 2B is a partial top view according to the first embodiment.

FIGS. 2A and 2B show a first embodiment 10'. In this embodiment, a plurality of biomagnets 20 which may be multi-pole biomagnets or north/south pole biomagnets, preferably having the north pole oriented toward the body, are provided in the temples 40 of the eyewear. According to this embodiment, the biomagnets are provided substantially equally spaced as shown along a substantial portion of the overall length of the temples. For example, four biomagnets may be used. Although four biomagnets are shown, other numbers of biomagnets can be provided. The biomagnets can be affixed to the temples or molded integrally in the temples.

FIGS. 3A and 3B show a second embodiment 10" according to the present invention in which a strip biomagnet 30 is provided in the temples 40'. The strip biomagnet preferably extends over a substantial length of the temple. Preferably, the strip biomagnet may be a multi-pole biomagnet or it preferably has the north pole oriented toward the body.

According to the first two embodiments, the biomagnets can be made integrally with the temples, in this case, temples which are made of a molded material such as plastic or rubber. However, the biomagnets can also be used on metal frame eyewear. In addition, although the biomagnets in FIGS. 2A, 2B, 3A and 3B are preferably integrally molded, the biomagnets can be affixed externally to the temples by a known means, such as adhesive soldering, welding etc. Also, although the biomagnets may be provided on or in both temples, the biomagnet or biomagnets can be provided in or on only one temple.

Figure 4B:
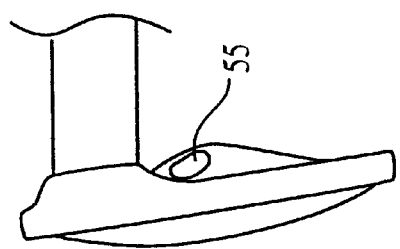
FIG. 4B shows a partial side view of the third embodiment.
Figure 4A:
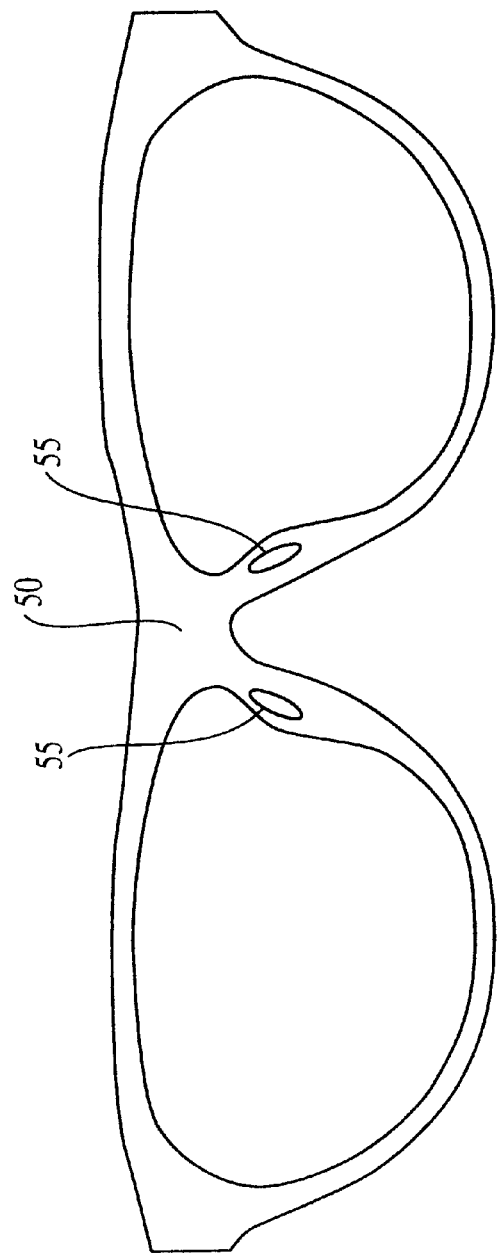
FIG. 4A shows a front view of a third embodiment according to the present invention.

FIGS. 4A and 4B show a third embodiment in which the biomagnets are provided near the bridge 50 of the eyewear and, in particular, in the embodiment shown, in the molded-in nose pad 55 of the eyewear. In addition, the embodiment shown in FIGS. 4A and 4B may also have biomagnets provided in the temples of the eyewear. Preferably, the biomagnets are multi-pole or preferably have the north pole oriented toward the body.

Figure 5B:
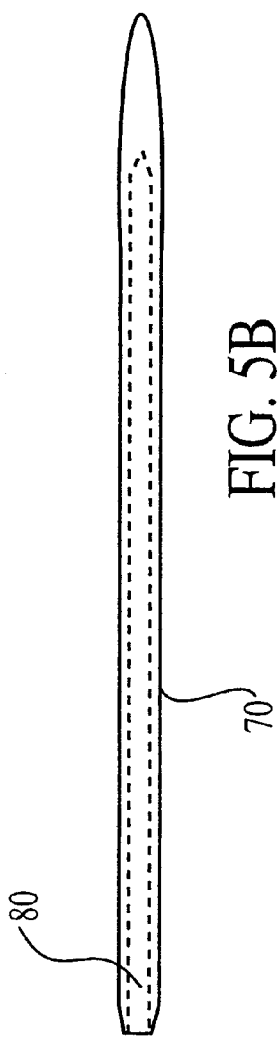
FIG. 5B is a top view of the embodiment of FIG. 5A.
Figure 5A:
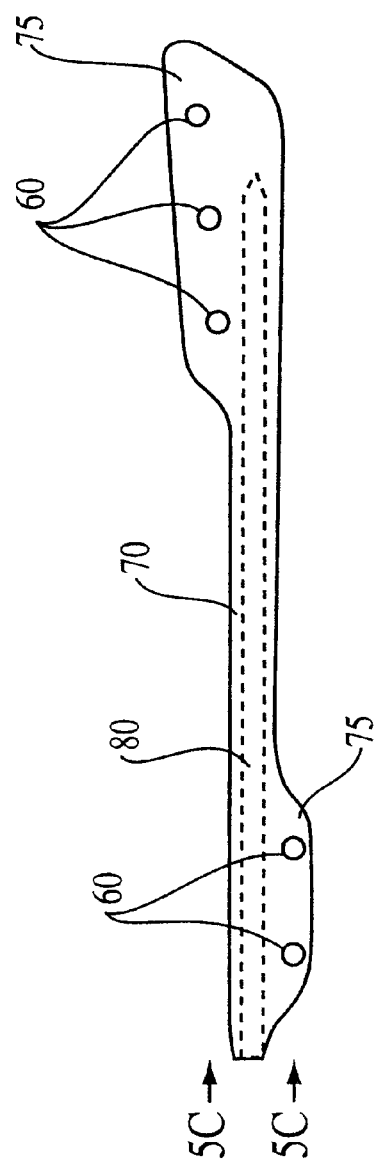
FIG. 5A shows a fourth embodiment of the present invention comprising temple tips which can be applied to a wearer's eyewear to provide the benefits of magnetic therapy.
Figure 5C:
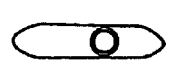
FIG. 5C is an end view taken along line C—C of FIG. 5A.

FIGS. 5A and 5B show a fourth embodiment in which the biomagnets 60, of which five are shown in FIG. 5A, are provided in temple tips 70 which are slidably received on the temples of the wearer's eyewear. The temple tips as shown in FIG. 5A include a plurality of biomagnets 60 preferably molded into the temple tips. The temple tips may be formed of plastic, rubber material or some other suitable material, and preferably a material which is pliable so that it can bend to conform to the temples of the wearer's eyewear. The temple tips include a longitudinally extending channel which 80 receives the temples of the wearer's eyewear. The temple tips according to the invention are particularly adapted to be used with metal frame eyewear, although they can be adapted to eyewear of other types. The temple tips according to FIGS. 5A and 5B can be provided on eyewear to retrofit eyewear which does not include biomagnets. In such case, the existing temple tips may be removed and the new temple tips slid onto the existing temples. The temple tips according to the invention may be secured to the temples using, for example, an adhesive. The temple tips can be bent to conform to the shape of the temples of the wearer's eyewear.

As shown, the temple tips may have enlarged regions 75 wherein the biomagnets are disposed.

FIG. 6 shows a temple tip according to the invention provided on a temple 90 of existing eyewear. Five biomagnets are shown.

Figure 7:
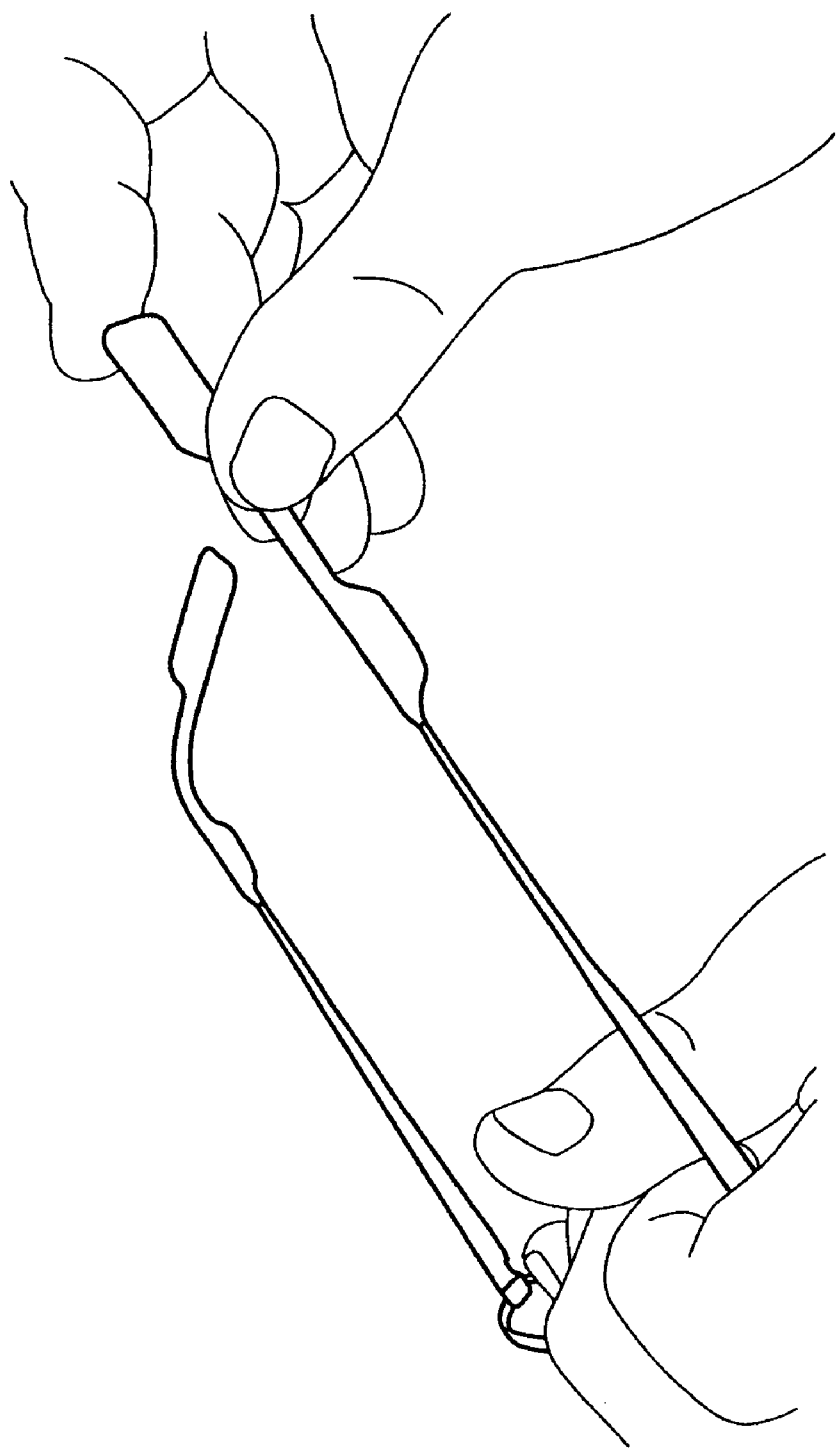
FIG. 7 shows how the temple tips are emplaced on the temples of the wearer's eyewear.

FIG. 7 shows how the temple tips 70 can be provided on the eyewear by sliding them onto the temples. The temple tips can thereafter be bent by hand to conform to the bends in the temples of the eyewear. If the temples are already bent, they can be straightened prior to installation of the temple tips and then rebent to the proper shape. Alternatively, because the temple tips are pliable, they can be applied and formed to already bent temples. Although a temple tip is typically to be attached to each of two temples, only one temple tip can be attached to a single temple tip of the eyewear.

Although the present invention has been described in relation to particular embodiments thereof, many other variations and modifications and other uses will become apparent to those skilled in the art. Therefore, the present invention should be limited not by the specific disclosure herein, but only by the appended claims.

What is claimed is:

1. Eyewear comprising:
   at least one lens for transmitting light energy to a wearer's eye,
   a frame for the lens;
   the frame including a pair of temples for supporting the frame on the wearer's ears, at least one of the temples including a plurality of substantially equally spaced biomagnets attached to the temples extending along each temple for providing a magnetic field to the wearer's head.

2. The eyewear of claim 1, wherein the biomagnets are multi-pole or have a north pole facing the head.

3. Eyewear comprising:
   at least one lens for transmitting light energy to a wearer's eye,
   a frame for the lens;
   the frame including a pair of temples for supporting the frame on the wearer's ears, at least one of the temples including a strip biomagnet provided along the longitudinal axis of the temple extending over at least half the length of each temple for providing a magnetic field to the wearer's head.

4. The eyewear of claim 3, wherein the biomagnet is multi-pole or has a north pole facing the head.

* * * * *